US00PP31136P2

(12) United States Plant Patent
Hansen

(10) Patent No.: US PP31,136 P2
(45) Date of Patent: Nov. 26, 2019

(54) **X *MANGAVE* PLANT NAMED 'NAVAJO PRINCESS'**

(50) Latin Name: ***Manfreda* times *Agave*, known as x *Mangave***
Varietal Denomination: Navajo Princess

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,481

(22) Filed: Nov. 20, 2018

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Mangave* plant named 'Navajo Princess' characterized by a medium mound of broad, semi-fleshy, longitudinally folded, stiff and upright to outright foliage. The variegated foliage has greyed-green centers with creamy white margins and a frosty green zone between, and with greyed-purple spots toward base that intensify with strong ultraviolet light. Leaves have small, flexible marginal teeth. The new plant is suitable for the garden or as a potted plant in the garden or home.

2 Drawing Sheets

Botanical classification: Hybrid; *Manfreda* times *Agave*, known as x *Mangave*.

Variety denomination: 'Navajo Princess'.

STATEMENT REGARDING PRIOR DISCLOSURES UNDER 37 CFR 1.77(b)(6)

The first public disclosure of the claimed plant, in the form of a sale, was made by Walters Gardens, Inc. on Nov. 27, 2017 to Plant Delights Nursery, Inc. in a private sale. Plants for this sale were obtained from the inventor. No plants of x *Mangave* 'Navajo Princess' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Navajo Princess' that was hybridized by the inventor at a wholesale perennial nursery in Zeeland, Mich., USA as a cross between an unreleased, unnamed, proprietary, variegated *Manfreda maculosa* (not patented) as the female or seed parent times an unnamed selection of *Agave montana* (not patented) as the male or pollen parent. The cross was performed on Apr. 1, 2014 and seeds were harvested and sown later on Jul. 1, 2014. Through trials at the same nursery the plant was assigned the breeder code 14-33-1. The new plant has been successfully asexually propagated first by removal of offsets and later by sterile shoot-tip tissue culture at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Navajo Princess' differs from its parents as well as all other *Manfreda, Agave* and x *Mangave* known to the applicant. The female parent has foliage that has a sectoral chimera variegation, with leaves that are narrower and more linear, flexible and arching, thinner in cross section, has smaller marginal teeth, leaves are more succulent, with more significant mahogany spotting and less arching. The male parent has larger habit and leaf size, has foliage that is more upright and more cupped toward apex, with larger marginal teeth, more fibrous, and no greyed-purple spotting. The nearest comparison plants are *Agave cordillerens* 'Benito' (not patented), *Agave desmetiana* 'Desert Sunset'(not patented), *Agave montana* 'Tiffany'(not patented) and x *Mangave* 'Kaleidoscope' U.S. Plant Pat. No. 28,614. 'Benito, 'Desert Sunset' and 'Tiffany' all have broader foliage with creamy margins, but without the greyed-purple spots and light pinkish tint in high ultraviolet exposure leaf areas. 'Kaleidoscope' has a variegated margin that is more yellowish than the new plant, the marginal teeth are smaller and more evenly spaced, the terminal spine is less pronounced and it has more flexible and less upright foliage and shows more reddish tinting and mahogany spotting than the new plant.

The new plant, 'Navajo Princess', is unique from all of the above cultivars and all *Agave*, x *Mangave* and *Manfreda* known to the inventor by the following combined traits:

1. Medium mound of lanceolate, semi-fleshy, foliage small flexible marginal teeth and flexible terminal spine;
2. Foliage has greyed-purple spots toward base that become more pronounced in strong ultraviolet light;
3. Leaves have creamy white margins with irregular frosty green zone between margin and deep-green center;

4. Moderate growth rate.
5. Foliage is upright to outright with a slightly cupped apex.

BRIEF DESCRIPTION OF THE DRAWING

The photograph of x *Mangave* 'Navajo Princess' demonstrates the overall appearance of the new plant including the unique traits as a four-year-old plant grown in a container in a greenhouse in Zeeland, Mich. with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
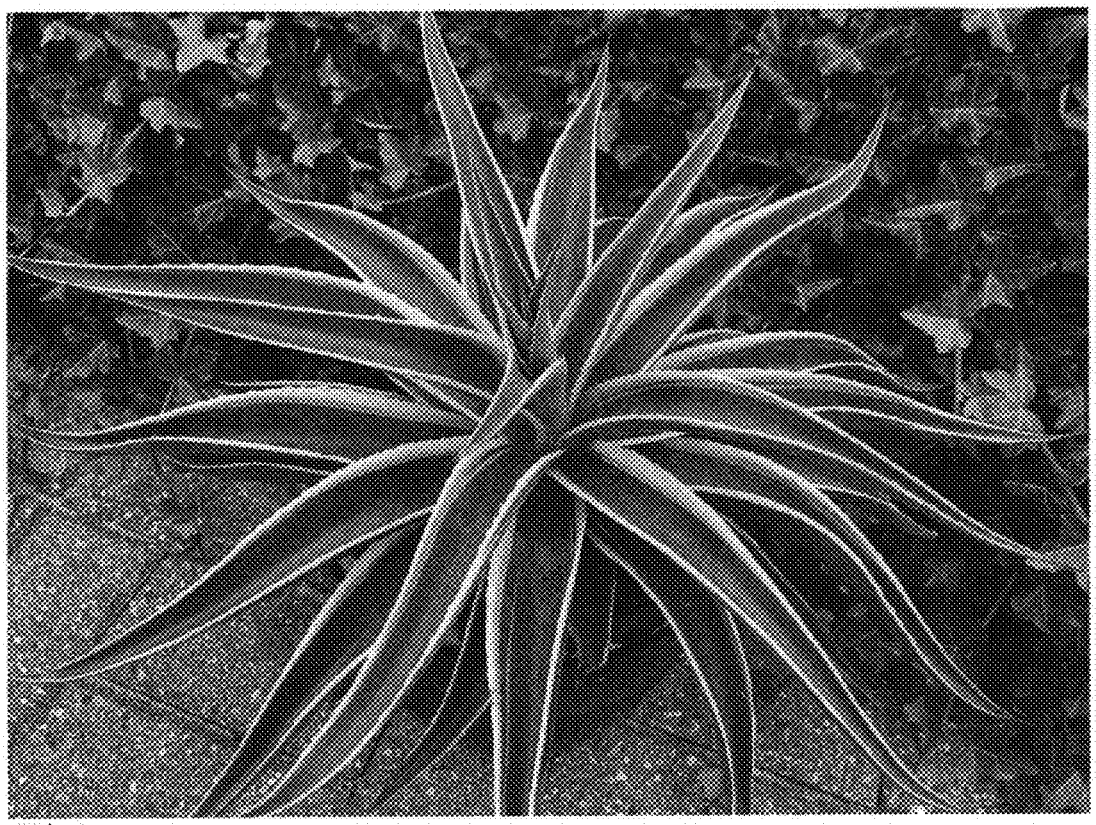
FIG. 1 shows a top view of a plant in a full-sun trial garden.
Figure 2:
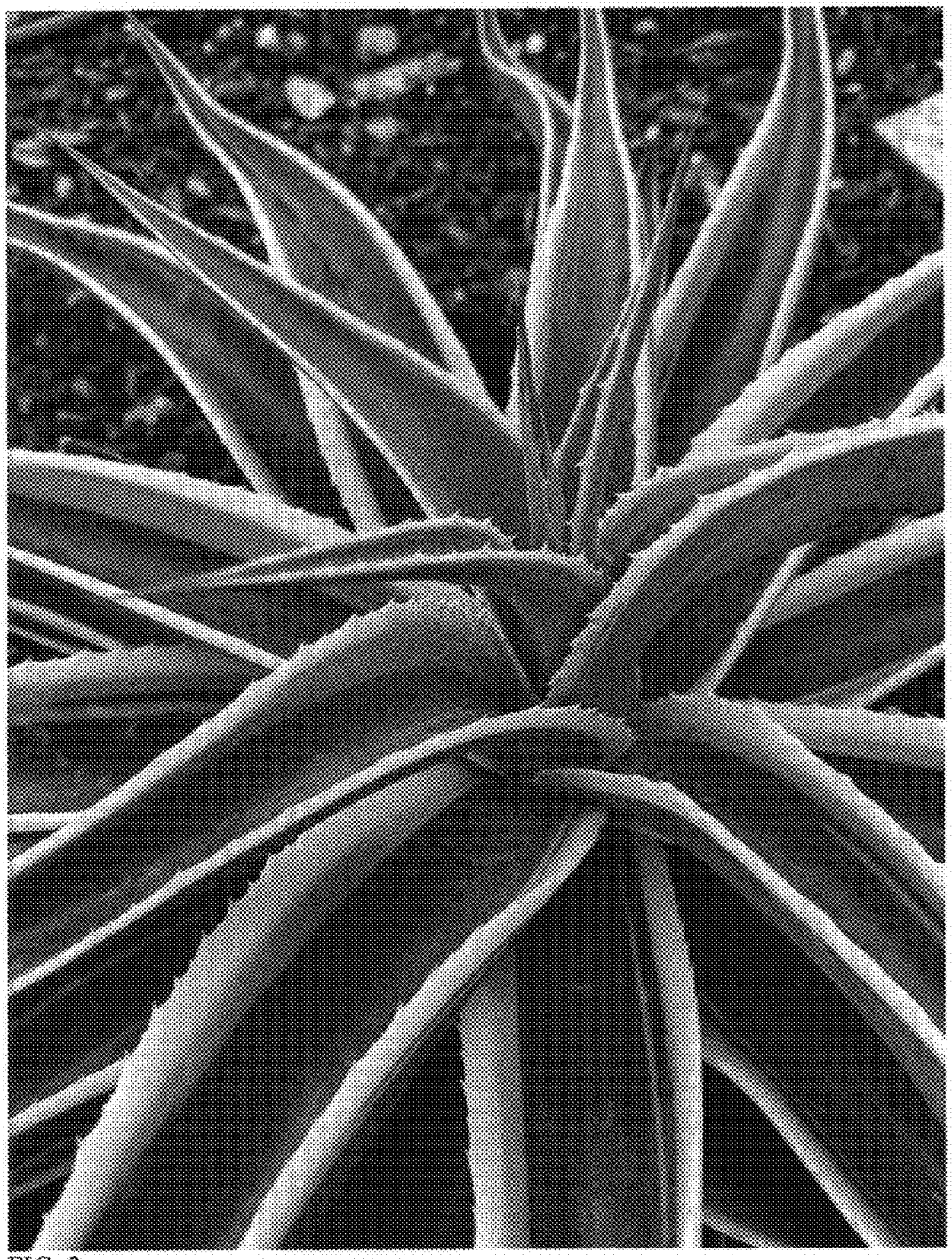
FIG. 2 shows a close-up of the foliage with sinuate margins and heavily folded leaves with small teeth.

The following descriptions and color references are based on the 2015 edition of The Royal Horticultural Society Colour Chart except where common dictionary terms are used. The new plant, x *Mangave* 'Navajo Princess', has not been observed under all possible environments. The phenotype may vary slightly with different environmental conditions, such as temperature, light, fertility, moisture and maturity levels, but without any change in the genotype. The following observations and size descriptions are of a four-year-old plant in a commercial wholesale greenhouse and in a full-sun trial garden in Zeeland, Mich. with supplemental water and fertilizer as needed.

Parentage: The female or seed parent is an unnamed proprietary variegated seedling of *Manfreda maculosa*, and the male or pollen parent is an unnamed select form of *Agave montana;*

Propagation: By sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 20 cm long;

Root color: Nearest RHS 158C;

Plant shape and habit: Succulent herbaceous perennial with basal rosettes of about 40 leaves radially emerging outwardly from central stem, producing a radially-symmetrical, rounded mound;

Plant size: Foliage height about 25.5 cm tall from soil line to the top of the leaves and about 76.2 cm wide at the widest point slightly above the soil line in container or in test garden;

Foliage description: Lanceolate; simple; sessile; bi-laterally symmetrical; apex narrowly acute with terminal spine; terminal flexible spine to about 10.0 mm long; base truncate; slightly conduplicate to cupped in distal 3.0 cm; margins flat; margins finely dentate with soft flexible teeth; glabrous and slightly glaucous abaxial and adaxial, lustrous abaxial and adaxial with age; with abaxial and adaxial spots about 2.0 mm to 7.0 mm long and wide frequently touching or overlapping especially toward proximal center;

Teeth: Flexible; about 2.0 mm long and 2.0 mm wide at base of tooth and about 6.5 mm apart on mature leaves;

Leaf size: To about 30.0 cm long, about 6.4 cm wide toward base, about 1.8 cm deep near base and flattening toward middle, apex cupped about 0.5 cm deep; about 4.0 mm thick at basal midrib; average about 19.0 cm long, 3.5 cm wide and 4.0 mm thick; margin to about 15.0 mm wide in broadest leaf region;

Foliage fragrance: None observed;

Leaf number: About 52 per plant;

Leaf blade color:

*Adaxial* (*young*).—Margin nearest RHS 11D and center between RHS 138B and RHS N138D.

*Abaxial* (*young*).—Margin nearest RHS 11D and center between RHS 138B and RHS N138D.

*Adaxial* (*mature*).—Margin nearest RHS 11C with spots of about 2.0 mm diameter between RHS 186A and RHS 186B concentrated proximally, center between RHS 137A and NN 137A with spots to about 3.0 mm diameter of nearest RHS N186C concentrated proximally, an intermediate longitudinal zone between margin and center of between RHS 194B and lighter than RHS N138D; rarely a longitudinal line running part way from the center into the intermediate zone, or a line running part way from the margin into the center with colors the same as the zone of origin.

*Abaxial* (*mature*).—Margin nearest RHS 11C, center nearest RHS 137A, with rare longitudinal lines running part way from the center into the intermediate zone, or a line running part way from the margin into the center with colors the same as the zone of origin.

*Teeth*.—Adaxial and abaxial nearest RHS 11D with blush or nearest RHS 186B in proximal region.

Petiole: Leaves sessile;

Veins: Parallel; not distinct abaxial or adaxial; same color as surrounding leaf;

Flower description: Not yet observed;

Fruit and seed not observed;

Disease resistance: x *Mangave* 'Navajo Princess' has not been observed to be resistant to diseases beyond that which is normal for x *Mangave, Agave* or *Manfreda*. The new plant is xeromorphic and survives well with minimal water once established. The new plant is estimated to be hardy at least from USDA zone 7b. Full extent of winter hardiness has not been tested.

It is claimed:

1. A new and distinct cultivar of ornamental x *Mangave* plant named 'Navajo Princess' as herein described and illustrated.

* * * * *